United States Patent [19]
Igi et al.

[11] Patent Number: 5,389,637
[45] Date of Patent: Feb. 14, 1995

[54] 2-FORMYLAMINO-6-HALOGENOPURINE

[75] Inventors: Masami Igi, Osaka; Taketo Hayashi, Yao, both of Japan

[73] Assignee: Sumika Fine Chemicals Co., Ltd., Osaka, Japan

[21] Appl. No.: 115,015

[22] Filed: Sep. 2, 1993

Related U.S. Application Data

[62] Division of Ser. No. 937,427, Aug. 31, 1992.

[30] Foreign Application Priority Data

Nov. 22, 1991 [JP]  Japan ................... 3-334053

[51] Int. Cl.$^6$ ............................ C07D 473/40
[52] U.S. Cl. ..................... 544/277; 544/118
[58] Field of Search ........................ 544/277

[56]  References Cited

U.S. PATENT DOCUMENTS 4,736,029  4/1988  Harnden et al. .
5,017,701  5/1991  Grinter et al. ................... 544/277

FOREIGN PATENT DOCUMENTS 0203685  12/1986  European Pat. Off. .
0433846   6/1991  European Pat. Off. .
8133396   8/1981  Japan .
60-58982   4/1985  Japan .
60-208954 10/1985  Japan .
61-137886  6/1986  Japan .
61-227583 10/1986  Japan .
259583    2/1990  Japan .
767216    1/1957  United Kingdom .
9213859   8/1992  WIPO .

OTHER PUBLICATIONS

Shengwu Huaxue Yu, Shengwu Wuli Jinzhan, 1987(2), 62–64 (Abstract).
Beaman et al. (1962) J. Org. Chem. 27:986–990.
Koda et al. (1968) J. Pharm. Sci. 57:2056–2061.
Kiburis et al. (1971) J. Chem. Soc. 3942–3947.
Geen et al. (1990) Tetrahedron vol. 46, No. 19:6903–6914.
J. Am. Chem. Soc. 77, 1976(1955) (Abstract).
J. Am. Chem. Soc. 79, 2185–2188 (1957) (Abstract).
J. Am. Chem. Soc. 82, 2633–2640 (1960) (Abstract).
J. Org. Chem. 25, 1573–1575 (1960) (Abstract).
J. Heterocycl. Chem. 1974, 11(1), 77–8 (Abstract).
Khim. Geterotsikl, Soedin., 1970, (4) 529–533 (Abstract).

Primary Examiner—Robert W. Ramsuer
Attorney, Agent, or Firm—Birch, Stewart, Kolasch & Birch

[57]  ABSTRACT

The present invention is directed to a method for production of a 2-amino-6-halogenopurine, a novel synthesis intermediate therefor and a method for production of said synthesis intermediate. The desired 2-amino-6-halogenopurine is an intermediate for the production of compounds useful as antiviral agents, and by using the compound of the present invention as a starting material, the 2-amino-6-halogenopurine can be produced in high yield.

1 Claim, No Drawings

2-FORMYLAMINO-6-HALOGENOPURINE

This application is a divisional of copending U.S. patent application Ser. No. 07/937,427, filed on Aug. 31, 1992, allowed the entire contents of which are hereby incorporated by reference.

FIELD OF THE INVENTION

The present invention relates to a method for production of a 2-amino-6-halogenopurine and a synthesis intermediate therefor, more specifically to a method for production of a 2-amino-6-halogenopurine useful as an intermediate for further synthesizing a compound useful as an antiviral agent, and a synthesis intermediate therefor.

BACKGROUND OF THE INVENTION 2-amino-6-halogenopurine is known as a useful intermediate for producing guanine nucleoside analogues, as described in Japanese Patent Examined Publication No. 33396/1981, Japanese Patent Laid-Open Nos. 58982/1985, 208954/1985, 59583/1990, 108788/1992 and other publications.

For synthesizing such a 2-amino-6-halogenopurine, some methods have already been developed. Methods for forming a 6-chloro derivative include a method wherein guanine is reacted with phosphorus pentasulfide to introduce a mercapto group to the 6-position of the purine ring, followed by chlorine sparging, to give a 6-chloro derivative (method 1) (British Patent No. 767,216; J. Am. Chem. Soc. 77, 1676). However, in this method, the decomposition product of the phosphorus pentasulfide used generates a strong odor so that there is a fear for environmental pollution. Also, the yield is unsatisfactory, and this compound is dangerous in that the resulting thioguanine is mutagenic. Another method wherein 2-amino-6-mercaptopurine is reacted with methyl iodide to give a 6-methylthio derivative, followed by chlorine sparging, to give a 6-chloro derivative has been known (method 2) (J. Am. Chem. Soc. 79, 2185-2188; J. Am. Chem. Soc. 82, 2622-2640), but this method also involves the same risk as described in the method 1, because it also uses thioguanine as a starting material.

A still another method wherein guanine is reacted with phosphorus oxychloride in the presence of a quaternary ammonium salt to directly synthesize a 6-chloro derivative has been reported (method 3) (Japanese Patent Laid-Open No. 227583/1986). However, this method is not economically advantageous because the quaternary ammonium salt is expensive and the yield is as low as 30 to 42% due to the poor solubility of guanine.

Methods for forming a 6-bromo derivative include a method wherein thioguanine is reacted with bromine to give a 6-bromo derivative (J. Org. Chem., 27, 986, 1962); and methods for forming a 6-iodo derivative include a method wherein thioguanine is reacted with chlorine to give a 6-chloro derivative, which is then reacted with hydrogen iodide to yield an iodo derivative (J. Pharm. Sci., 57, 2056, 1968). However, all these methods can cause environmental pollution because of the strong odor of the decomposition product of the phosphorus pentasulfide used to produce the starting material thioguanine as above, and they are not economically advantageous in that the overall yield involving the desired product 2-amino-6-halogenopurine is low and operation is troublesome.

SUMMARY OF THE INVENTION

It is an object of the present invention to provide a method for production of a 2-amino-6-halogenopurine. It is another object of the present invention to provide a novel intermediate for said production method and a method for production of said intermediate.

Through investigations in search for a totally different production method free of the above problems, the present inventors have discovered a novel synthesis intermediate and found that the desired 2-amino-6-halogenopurine can be synthesized in high yield from this intermediate. The inventors have made further investigations based on these findings, and thus developed the present invention.

Specifically, the present invention essentially relates to the following:

(1) a compound represented by Formula (1):

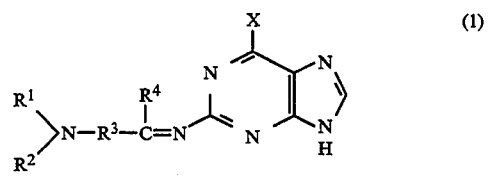

wherein $R^1$ and $R^2$ represent, respectively, a hydrogen atom, an alkyl group having 1 to 5 carbon atoms or an aromatic group, or they may form a ring, which may contain a nitrogen atom, an oxygen atom or a sulfur atom together with the N group; $R^4$ represents a hydrogen atom, an alkyl group having 1 to 5 carbon atoms or an aromatic group; $R^3$ represents a single bond or an alkylene group having 1 to 5 carbon atoms; and X represents a chlorine atom, a bromine atom, an iodine atom or a fluorine atom;

(2) a method for production of the compound represented by Formula (1), comprising reacting guanine with a compound represented by Formula (3) in the presence of a halogenating agent:

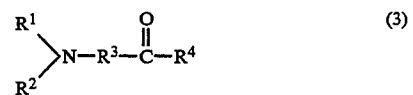

wherein $R^1$, $R^2$, $R^3$ and $R^4$ are as defined as above;

(3) a 2-formylamino-6-halogenopurine or a salt thereof represented by Formula (2):

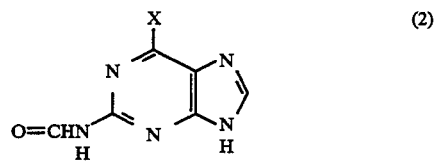

wherein X is as defined as above;

(4) a method for production of a 2-amino-6-halogenopurine, comprising hydrolyzing the compound represented by Formula (1); or hydrolyzing said compound under weakly acidic conditions to give a 2-formylamino-6-halogenopurine or a salt thereof, and further hydrolyzing the obtained compound to yield the desired product;

(5) a method for production of a 2-amino-6-halogenopurine, comprising reacting guanine with the compound represented by Formula (3) described above in the presence of a halogenating agent to give the compound represented by Formula (1), and then hydrolyzing said compound; or hydrolyzing said compound under weakly acidic conditions to give a 2-formylamino-6-halogenopurine or a salt thereof, and further hydrolyzing the obtained compound to yield the desired product;

(6) a compound represented by Formula (1'):

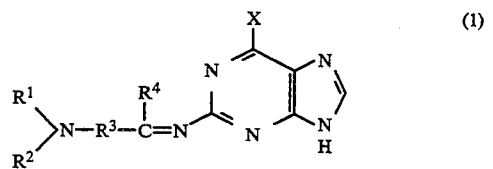

(1')

wherein $R^1$, $R^2$, $R^3$ and $R^4$ are as defined as above; and (7) a method for production of the compound represented by Formula (1'), comprising reacting guanine with the compound represented by Formula (3) in the presence of 0.5 to 2 mol of the halogenating agent per mol of said guanine.

DETAILED DESCRIPTION OF THE INVENTION

The synthesis intermediate used in the method for production of a 2-amino-6-halogenopurine of the present invention is (i) the compound represented by Formula (1); (ii) the 2-formylamino-6-halogenopurine represented by Formula (2) or a salt thereof obtained in the process for synthesizing a 2-amino-6-halogenopurine with the compound represented by Formula (1); and (iii) the compound represented by Formula (1') for synthesizing the compound represented by Formula (1).

First, the novel synthesis intermediate represented by Formula (1) and a method for production thereof are described below.

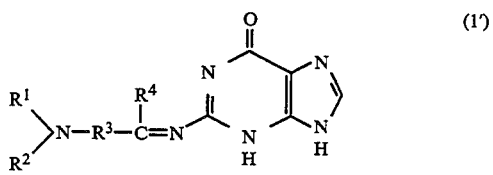

(1)

With respect to the compound represented by Formula (1), the group represented by $R^1$ or $R^2$ is a hydrogen atom, an alkyl group having 1 to 5 carbon atoms or an aromatic group, in which the alkyl group may be linear or branched, including a methyl group, an ethyl group, an n-propyl group and an isopropyl group. The aromatic group is exemplified by a phenyl group, etc. Also, the groups represented by $R^1$ and $R^2$ may form a ring with the N group. In this case, a nitrogen atom, an oxygen atom or a sulfur atom may be contained in one part of the ring.

The group represented by $R^4$ is a hydrogen atom, an alkyl group having 1 to 5 carbon atoms or an aromatic group. Examples of such alkyl groups or aromatic groups include the same groups as those specified above. $R^3$ represents a single bond or a linear alkylene group having 1 to 5 carbon atoms such as a methylene group, an ethylene group or a propylene group. Examples of the preferred compounds represented by Formula (1) having such substituents include a compound wherein $R^1$ and $R^2$ are both methyl groups, or one is a phenyl group and the other is a methyl group; $R^4$ is a hydrogen atom; and $R^3$ is a single bond, etc.

X represents a chlorine atom, a bromine atom, an iodine atom or a fluorine atom, with preference given to a chlorine atom or a bromine atom.

The compound represented by Formula (1) in the present invention is a novel synthesis intermediate obtained by reacting guanine with the compound represented by Formula (3) in the presence of a halogenating agent.

Examples of the halogenating agents which can be used herein include known chlorinating agents such as phosphorus oxychloride, thionyl chloride, sulfuryl chloride, phosphorus trichloride, phosphorus pentachloride, phosgene and diphosgene; known brominating agents such as phosphorus oxybromide, thionyl bromide, phosphorus tribromide and phosphorus pentabromide; known iodinating agents such as phosphorus triiodide; and known fluorinating agents such as phosphorus trifluoride and phosphorus oxyfluoride. In view of the reaction rate, phosphorus oxychloride is the preferred chlorinating agent.

With respect to the compound represented by Formula (3), the groups represented by $R^1$, $R^2$, $R^3$ and $R^4$ are exemplified by the same groups as specified for the compound represented by Formula (1). Specific compounds represented by Formula (3) include N,N-dimethylformamide, N,N-diethylformamide, N-methylformanilide, N,N-dimethylacetamide, N-formylpyrrolidine, N-formylpiperidine, N-formylpiperazine, N-formylmorpholine and N-formylthiomorpholine, with preference given to N,N-dimethylformamide and N-methylformanilide.

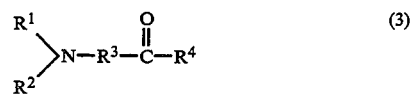

(3)

The compound represented by Formula (3) reacts with guanine in the presence of a halogenating agent, as described above. Although the present invention need not use a solvent, it is preferable to use an inert solvent from the viewpoint of improved operability. Examples of such solvents include dichloromethane, dichloroethane, chlorobenzene, dichlorobenzene, toluene, xylene and chloroform.

In the reaction of the process for producing the compound represented by Formula (1), a halogenating agent is used in an amount of usually 2 to 10 mol, preferably 2 to 5 mol, more preferably 2.5 to 3.5 mol per mol of guanine. Also, when a solvent is used, the amount of the compound represented by Formula (3) is usually 1 to 20 mol, preferably 3 to 10 mol, more preferably 4 to 6 mol per mol of guanine. When no solvent is used, the amount of the compound represented by Formula (3) is usually 5 to 30 mol, preferably 10 to 20 mol, more preferably 10 to 15 mol per mol of guanine. Lower amounts result in the yield reduction, and higher amounts are economically disadvantageous because the yield does not increase correspondingly.

When no solvent is used, the reaction temperature is usually 20 to 150° C., though it depends on the type of the compound represented by Formula (3). When N,N-dimethylformamide, for instance, is used, the reaction temperature is usually 80° to 120° C., and when N-methylformanilide is used, the reaction temperature is preferably in the range of 40° to 60° C. When a solvent is used, the reaction is carried out at a temperature near the boiling point thereof, and it is desirable not to exceed 120° C. from the viewpoint of the thermal stability of the compound represented by Formula (1). For example, when N,N-dimethylformamide or N-methylformanilide is used as the compound represented by Formula (3) and 1,2-dichloroethane as a solvent, the reaction temperature is preferably in the range from 70° to 85° C. The reaction is continued for usually 1 to 15 hours, preferably 3 to 10 hours, and more preferably 4 to 8 hours.

The thus-obtained compound represented by Formula (1) may be used in the next process after separation and purification. Alternatively, the reaction mixture may be used as such in the next process without separation and purification.

When the next process is carried out without separation and purification, the desired 2-amino-6-halogenopurine compound can be obtained by adding water to the reaction mixture, thereby hydrolyzing the compound represented by Formula (1) together with the residual reaction reagent. In this case, singe the addition of water to the reaction mixture results in the production of a strongly acidic substance as a by-product, hydrolysis can be achieved without adding a strongly acidic substance, etc. as specified in the following description of hydrolysis.

When the compound represented by Formula (1) is separated and purified, the desired compound can be obtained by cooling the reaction mixture and treating it with an aqueous solution of sodium hydrogen carbonate, sodium carbonate, potassium carbonate, sodium hydroxide, potassium hydroxide, etc. Although the compound represented by Formula (1) may be used as such in the next process, singe it can be obtained with a yield near to the theoretical calculation a known means such as filtration or recrystallization can be used appropriately to isolate it if there is a fear of the presence of a small amount of the by-product.

Next, the methods for production of the desired compound 2-amino-6-halogenopurine with the compound of Formula (1) thus obtained will be described below.

Two methods for the production of the desired compound 2-amino-6-halogenopurine by hydrolysis of the compound of Formula (1) are as follows:

Method (a): The compound represented by Formula (1), with or without separation and purification, is directly hydrolyzed.

Method (b): The separated and purified compound of Formula (1) is hydrolyzed under weakly acidic conditions to give a 2-formylamino-6-halogenopurine or a salt thereof, i.e., the compound of Formula (2), the novel synthesis intermediate of the present invention, followed by further hydrolysis.

In the method (a), a reaction temperature which is too low hampers hydrolysis, and a reaction temperature exceeding 20° C. results in an increased amount of guanine produced as a by-product. For this reason, the reaction is usually carried out at a temperature of 0° to 100° C. for 1 to 24 hours, preferably at a temperature of 10° to 20° C. for 10 to 20 hours to complete the reaction. In this case, in order to hydrolyze the separated and purified compound of Formula (1), it is preferable to hydrolyze it in the presence of a strongly acidic substance, a neutral substance or an alkaline substance. Examples of such substances include hydrochloric acid, sulfuric acid, phosphoric acid, p-toluenesulfonic acid, sodium hydroxide and potassium hydroxide. When using a reaction mixture containing the compound of Formula (1), which is not separated and purified, it is unnecessary to add a strongly acidic substance, etc. as described above.

In the method (b), the starting material is first hydrolyzed under weakly acidic conditions to give the 2-formylamino-6-halogenopurine represented by Formula (2) or a salt thereof. The 2-formylamino-6-halogenopurine or the salt thereof is a novel compound discovered for the first time in the present invention. The reaction is usually carried out at a temperature of 20° to 100° C. for 1 to 10 hours, preferably at a temperature of 50° to 70° C. for 3 to 5 hours to complete the reaction. Although any means can be used to obtain weakly acidic conditions without limitation, it is a common practice to add an acidic substance such as acetic acid, propionic acid or hydrochloric acid to obtain such conditions.

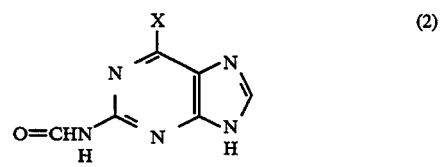

(2)

Next, further hydrolysis is carried out to yield the desired 2-amino-6-halogenopurine compound. The reaction is usually carried out at a temperature of 0° to 50° C. for 1 to 24 hours, preferably at a temperature of 5° to 30° C. for 2 to 20 hours. In the same manner as in method (a), it is preferable to carry out the hydrolysis in the presence of a strongly acidic substance, a neutral substance or an alkaline substance.

Of these methods, method (b) is advantageous over method (a) in that less guanine is produced as a by-product. The reaction product obtained by the hydrolysis comprises almost 100% of the desired 2-amino-6-halogenopurine compound in some cases and contains a small amount of guanine in other cases. In the latter case, the 2-amino-6-halogenopurine can be separated and purified by adding hot aqueous ammonia to the mixture and filtering out the insoluble substance guanine.

In one embodiment of the present invention, wherein $R^1$ and $R^2$ are both methyl groups, $R^3$ is a single bond, $R^4$ is a hydrogen atom and X is a chlorine atom, the desired 2-amino-6-chloropurine compound is synthesized by the following process.

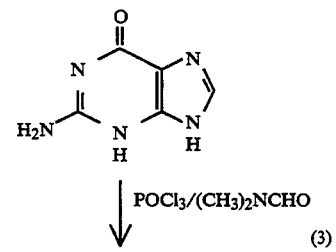

(3)

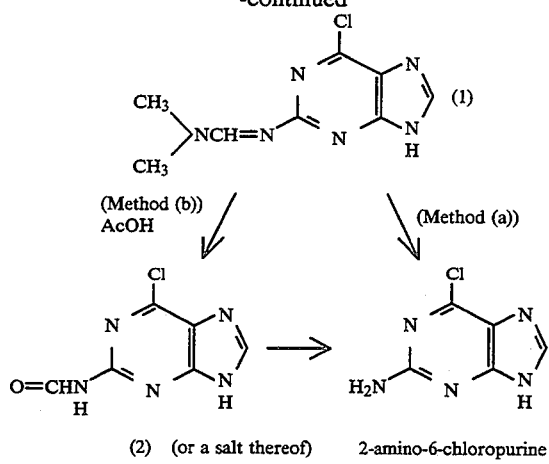

(2) (or a salt thereof)    2-amino-6-chloropurine

The 2-amino-6-halogenopurine, which can be thus produced with the compound represented by Formula (1), can be used as a synthesis intermediate for guanine nucleoside analogues which are useful as antiviral agents, as described in Japanese Patent Examined Publication No. 33396/1981, Japanese Patent Laid-Open Nos. 58982/1985, 208954/1985, 59583/1990 and 108788/1992 and other publications.

In the present invention, the desired 2-amino-6-halogenopurine compound is synthesized from the starting material guanine by using the compound represented by Formula (1) as an intermediate, and this compound represented by Formula (1) may be synthesized with the compound represented by the following Formula (1').

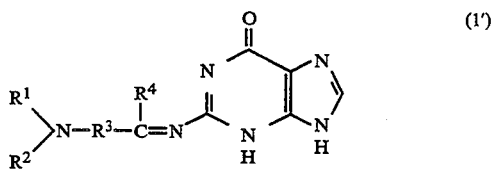

With respect to Formula (1'), the groups represented by $R^1$, $R^2$, $R^3$ and $R^4$ are exemplified by the same groups as specified for the compound represented by Formula (1). The compound represented by Formula (1') of the present invention is a novel synthesis intermediate obtained by reacting guanine with the compound represented by Formula (3) in the presence of a halogenating agent. Examples of the halogenating agents which can be used herein include the same halogenating agents as those used to synthesize the compound represented by Formula (1). When using a chlorinating agent, for instance, preference is given to phosphorus oxychloride and thionyl chloride in view of the reaction rate.

In the reaction of the process for producing the compound represented by Formula (1'), a halogenating agent is usually used in an amount of 0.5 to 2 mol, preferably 1 to 1.5 mol, more preferably 1.1 to 1.5 mol per mol of guanine. An amount lower than 0.5 mol results in reduction of the reaction rate and an amount exceeding 2 mol results in reduction in the yield of the compound represented by Formula (1'), leading to the direct yield of the compound represented by Formula (1). Also, when a solvent is used, the amount of the compound represented by Formula (3) is usually 1 to 20 mol, preferably 3 to 10 mol, more preferably 4 to 6 mol per mol of guanine. When no solvent is used, the amount of the compound represented by Formula (3) is usually 5 to 30 mol, preferably 10 to 20 mol, more preferably 10 to 15 mol per mol of guanine. Lower amounts result in a reduction in yield and higher amounts are economically disadvantageous because the yield does not increase correspondingly.

The compound represented by Formula (3) reacts with guanine in the presence of a halogenating agent, as described above. Although the present invention need not use a solvent, it is preferable to use an inert solvent from the viewpoint of improved operability. Examples of such solvents include dichloromethane, dichloroethane, chlorobenzene, dichlorobenzene, toluene, xylene and chloroform.

When no solvent is used, the reaction temperature is usually 20° to 150° C., though it depends on the type of the compound represented by Formula (3). When N,N-dimethylformamide, for instance, is used, the reaction temperature is preferably in the range of 80° to 120° C., and when N-methylformanilide is used, the reaction temperature is preferably in the range of 40° to 60° C. When a solvent is used, the reaction is carried out at a temperature near the boiling point thereof, and it is desirable not to exceed 120° C. from the viewpoint of the thermal stability of the compound represented by Formula (1'). For example, when N,N-dimethylformamide or N-methylformanilide is used as the compound represented by Formula (3) and 1,2-dichloroethane as a solvent, the reaction temperature is preferably in the range from 70° to 85° C. The reaction is continued for usually 1 to 15 hours, preferably 3 to 10 hours, more preferably 4 to 8 hours.

The compound represented by Formula (1') thus obtained is an intermediate useful for the production of the compound represented by Formula (1), and the compound represented by Formula (1) can be produced by halogenating the compound represented by Formula (1').

The above reaction is carried out by reacting a halogenating agent, whose examples may be the same as those used for directly synthesizing the compound represented by Formula (1) from guanine as described above, by the use of an organic solvent such as N,N-dimethylaniline, N,N-diethylaniline, N,N-dimethylformamide or 1,2-dichloroethane, with preference given to N,N-dimethylaniline. A preferred example of a chlorinating agent includes phosphorus oxychloride from the viewpoint of the reaction rate. In this case, the halogenating agent is used in an amount of usually 1 to 10 mol, preferably 1 to 5 mol, more preferably 2 to 3 mol per mol of the compound represented by Formula (1'). When the amount of the halogenating agent used is lower than 1 mol, the yield of the resulting compound represented by Formula (1) is reduced, and when it exceeds 10 mol, it is economically disadvantageous because the yield does not increase correspondingly. Although the reaction temperature depends on the solvent used, the reaction temperature is usually in the range of 50° to 120° C. For example, when N,N-dimethylaniline is used as a solvent, the reaction temperature is preferably in the range of 70° to 90° C. The reaction is continued for usually 1 to 10 hours, preferably 1 to 5 hours, more preferably 2 to 3 hours to complete the reaction.

By using the synthesis intermediate represented by Formula (1) found by the present invention as a starting material, the desired 2-amino-6-halogenopurine can be synthesized in high yield. This method is economically advantageous because the minor starting material is inexpensive.

EXAMPLES

The present invention is hereinafter described in more detail by means of the following working examples and comparative examples, which are not to be construed as limitative.

EXAMPLE 1

46.0 g (0.3 mol) of phosphorus oxychloride was added to 73.1 g (1.0 mol) of N,N-dimethylformamide, and 15.1 g (0.1 mol) of guanine (manufactured by Sumika Fine Chemicals Co., Ltd.) was then added, followed by stirring at 100° C. for 4 hours. After cooling, 100 ml of water was carefully added at 20° C. After stirring at room temperature for 24 hours, the precipitating crystal was collected by filtration and dissolved in 100 ml of 25% aqueous ammonia with heating, and the insoluble substances were filtered out. The mother liquor was concentrated under reduced pressure, and the precipitating crystal was collected by filtration to yield 9.3 g (0.055 mol) of a white crystal of 2-amino-6-chloropurine (yield 55%).

EXAMPLE 2

115.0 g (0.75 mol) of phosphorus oxychloride was added to 263.1 g (3.6 mol) of N,N-dimethylformamide, and 45.3 g (0.3 mol) of guanine (manufactured by Sumika Fine Chemicals Co., Ltd.) was then added, followed by stirring at 100° C. for 5 hours. After cooling, the reaction mixture was added to 1500 ml of water containing 315.0 g (3.75 mol) of sodium hydrogen carbonate. The precipitating crystal was collected by filtration and washed with 500 ml of water to yield a crystal of 2-dimethylaminomethyleneamino-6-chloropurine, whose properties are as follows:

Melting point: 300° C. (Decomposition)
Elemental analysis:
Found value: C: 42.85%, H: 4.18%, N: 37.05%, Cl: 15.93%
Calculated value: C: 42.77%, H: 4.04%, N: 37.41%, Cl: 15.78%
MS: 224(M+), 209, 189, 168

The resulting crystal of 2-dimethylaminomethyleneamino-6-chloropurine was added to 250.0 g (2.40 mol) of 35% hydrochloric acid, followed by stirring at 15° C. for 20 hours. The crystal was collected by filtration and washed with 50 ml of methanol.

The crystal thus obtained was dissolved in 300 ml of 25% aqueous ammonia with heating and treated with 5.0 g of activated charcoal. The mother liquor was concentrated under reduced pressure, and the precipitating crystal was collected by filtration to yield 30.5 g (0.18 mol) of a white crystal of 2-amino-6-chloropurine (yield 60%).

EXAMPLE 3

A crystal of 2-dimethylaminomethyleneamino-6-chloropurine obtained in the same manner as in Example 2 was added to 78.1 g (1.3 mol) of acetic acid, followed by stirring at 60° C. for 4 hours. A part of the reaction mixture was analyzed for its properties, and it was identified as 2-formylamino-6-chloropurine. Its properties are as follows:

Melting point: not less than 300° C. (Decomposition)
Elemental analysis:
Found value: C: 36.45%, H: 2.10%, N: 35.40%, Cl: 18.15%
Calculated value: C: 36.47%, H: 2.04%, N: 35.45%, Cl: 17.94%
MS: 197(M+), 168, 153, 119

Next, this reaction mixture was cooled to 5° C., and 218.8 g (2.1 mol) of 35% hydrochloric acid was added, followed by stirring at 10° C. for 12 hours. The resulting crystal was collected by filtration and washed with 50 ml of methanol.

The crystal thus obtained was dissolved in 300 ml of 25% aqueous ammonia with heating and treated with 5.0 g of activated charcoal. The mother liquor was concentrated under reduced pressure, and the precipitating crystal was collected by filtration to yield 33.0 g (0.195 mol) of a white crystal of 2-amino-6-chloropurine (yield 65%).

EXAMPLE 4

A crystal of 2-dimethylaminomethyleneamino-6-chloropurine obtained in the same manner as in Example 2 was added to 650 ml of a 12% aqueous solution of acetic acid, followed by stirring at 70° C. for 3 hours. The precipitating crystal was collected by filtration and washed with water to yield 2-formylamino-6-chloropurine acetate. This crystal was then dissolved in a 10% aqueous solution of sodium hydroxide and stirred at room temperature for 2 hours, followed by neutralization with 35% hydrochloric acid. The precipitating crystal was collected by filtration and washed with water to yield 35.6 g (0.21 mol) of a white crystal of 2-amino-6-chloropurine (yield 70%).

EXAMPLE 5

45.3 g (0.3 mol) of guanine (manufactured by Sumika Fine Chemicals Co., Ltd.) was added to 490.5 g (3.6 mol) of N-methylformanilide, and then 138.0 g (0.9 mol) of phosphorus oxychloride was added drop by drop, followed by stirring at 50° C. for 5 hours. After cooling, the reaction mixture was neutralized with 217.5 g (2.05 mol) of sodium carbonate, while dropping it into 1500 ml of water. The precipitating crystal was collected by filtration and washed with water to yield a crystal of 2-phenylmethylaminomethyleneamino-6-chloropurine. Its properties are as follows:

Melting point: 223° C. (Decomposition)
Elemental analysis:
Found value: C: 54.54%, H: 3.90%, N: 29.31%, Cl: 12.25%
Calculated value: C: 54.46%, H: N: 29.30%, Cl: 12.36%
MS: 269(M+), 243, 209, 168

Next, the crystal of 2-phenylmethylamino-6-chloropurine was treated in the same manner as in Example 4 to yield 38.2 g (0.225 mol) of a white crystal of 2-amino-6-chloropurine (yield 75%).

EXAMPLE 6

131.6 g (1.8 mol) of N,N-dimethylformamide and 138.0 g (0.9 mol) of phosphorus oxychloride were added to 500 ml of 1,2-dichloroethane, and then 45.3 g (0.3 mol) of guanine (manufactured by Sumika Fine Chemicals Co., Ltd.) was added, followed by stirring at 80° C. for 8 hours. After cooling, the reaction mixture was added to 1200 ml of water. Next, 175.6 g (1.65 mol) of sodium carbonate was added to adjust the water layer to a pH of 4. After stirring for 30 minutes, the mixture was kept standing, and the water layer was separated. 25.2 g (0.63 mol) of sodium hydroxide was gradually added. The precipitating crystal was collected by filtration and washed with 200 ml of water to yield 60.7 g (0.27 mol) of a crystal of 2-dimethylaminomethyleneamino-6-chloropurine, which was then treated in the same manner as in Example 4 to yield 35.6 g (0.21 mol) of a white crystal of 2-amino-6-chloropurine (yield 70%).

EXAMPLE 7

The reaction is carried out in the same manner as in Example 1 except that 187.4 g (0.9 mol) of phosphorus pentachloride is used in the place of phosphorus oxychloride as a chlorinating agent to yield a white crystal of 2-amino-6-chloropurine.

EXAMPLE 8

The reaction is carried out in the same manner as in Example 2 except that N,N-diethylformamide or N-formylpiperidine is used in the place of N,N-dimethylformamide to yield, respectively, a crystal of 2-diethylaminomethyleneamino-6-chloropurine or 2-piperidinomethyleneamino-6-chloropurine as an intermediate for further synthesis. A further treatment is carried out in the same manner as in Example 2 on these crystals to yield a white crystal of 2-amino-6-chloropurine.

EXAMPLE 9

The reaction is carried out in the same manner as in Example 6 except that chlorobenzene is used in the place of 1,2-dichloroethane to yield a white crystal of 2-amino-6-chloropurine.

EXAMPLE 10

86.0 g (0.3 mol) of phosphorus oxybromide was added to 73.1 g (1.0 mol) of N,N-dimethylformamide, and 15.1 g (0.1 mol) of guanine (manufactured by Sumika Fine Chemicals Co., Ltd.) was then added, followed by stirring at 100° C. for 4 hours. After cooling, 200 ml of water was carefully added at 20° C. After stirring at room temperature for 24 hours, the precipitating crystal was collected by filtration and dissolved in 200 ml of 25% aqueous ammonia with heating, and the insoluble substances were filtered out. The mother liquor was concentrated under reduced pressure, and the precipitating crystal was collected by filtration to yield 11.1 g (0.052 mol) of a pale yellow crystal of 2-amino-6-bromopurine (yield 52%). Its properties are as follows:

Elemental analysis:
Found value: C: 28.06%, H: 1.88%, N: 32.72%, Br: 37.33%
Calculated value: C: 27.89%, H: 1.75%, N: 32.95%, Br: 37.42%

EXAMPLE 11

203.0 g (0.75 mol) of phosphorus tribromide was added to 263.1 g (3.6 mol) of N,N-dimethylformamide, and 45.3 g (0.3 mol) of guanine (manufactured by Sumika Fine Chemicals Co., Ltd.) was then added followed by stirring at 100° C. for 8 hours. After cooling, the reaction mixture was added to 2000 ml of water containing 315.0 g (3.75 mol) of sodium hydrogen carbonate. The precipitating crystal was collected by filtration and washed with 500 ml of water to yield a crystal of 2-dimethylaminomethyleneamino-6-bromopurine, whose properties are as follows:

Elemental analysis:
Found value: C: 35.71%, H: 3.37%, N: 31.23%, Br: 29.69%
Calculated value: C: 35.90%, H: 3.27%, N: 31.40%, Br: 29.45%

The resulting crystal of 2-dimethylaminomethyleneamino-6-bromopurine was added to 647.3 g (2.40 mol) of 30% hydrobromic acid, followed by stirring at 15° C. for 20 hours. The crystal was collected by filtration and washed with 50 ml of methanol.

The crystal thus obtained was dissolved in 500 ml of 25% aqueous ammonia with heating and treated with 5.0 g of activated charcoal. The mother liquor was concentrated under reduced pressure, and the precipitating crystal was collected by filtration to yield 37.2 g (0.17 mol) of a pale yellow crystal of 2-amino-6-bromopurine (yield 58%). The results of LC and UV for the obtained crystal were consistent with those of products in Example 10.

EXAMPLE 12

A crystal of 2-dimethylaminomethyleneamino-6-bromopurine obtained in the same manner as in Example 11 was added to 78.1 g. (1.3 mol) of acetic acid, followed by stirring at 60° C. for 4 hours. A part of the reaction mixture was analyzed for its properties, and it was identified as 2-formylamino-6-bromopurine. Its properties are as follows:

Elemental analysis:
Found value: C: 81.88%, H: 1.78%, N: 30.98%, Br: 35.35%
Calculated value: C: 31.82%, H: N: 31.00%, Br: 35.58%

Next, this reaction mixture was cooled to 5° C., and 566.4 g (2.1 mol) of 30% hydrobromic acid was added, followed by stirring at 10° C. for 12 hours. The resulting crystal was collected by filtration and washed with 50 ml of methanol.

The crystal thus obtained was dissolved in 500 ml of 25% aqueous ammonia with heating and treated with 5.0 g of activated charcoal. The mother liquor was concentrated under reduced pressure, and the precipitating crystal was collected by filtration to yield 40.5 g (0.19 mol) of a pale yellow crystal of 2-amino-6-bromopurine (yield 63%). The results of LC and UV for the obtained crystal were consistent with those of products in Example 10.

EXAMPLE 13

The reaction was carried out in the same manner as in Example 12 except that phosphorus triiodide was used in place of phosphorus tribromide to yield a pale yellow crystal of 2-amino-6-iodopurine at a yield of 47%. Its properties are as follows:

Elemental analysis:
Found value: C: 23.00%, H: 1.54%, N: 26.83%, I: 48.62%
Calculated value: C: 22.85%, H: 1.63%, N: 26.61%, I: 48.88%

EXAMPLE 14

15.1 g (0.1 mol) of guanine (manufactured by Sumika Fine Chemicals Co., Ltd.) was added to 175.4 g (2.4 mol) of N,N-dimethylformamide, and then 23.0 g (0.15 mol) of phosphorus oxychloride was added drop by drop, followed by stirring at 30° C. for 1 hour. The reaction mixture was added to 500 ml of ice water, and then neutralized with 75.6 g (0.9 mol) of sodium hydrogen carbonate. The precipitating crystal was collected by filtration and washed with 50 ml of water to yield 14.6 g (0.07 mol) of a white crystal of N-dimethylaminomethyleneguanine (yield 71%). Its properties are as follows:

Melting point: 289° C. (Decomposition)
Elemental analysis:
Found value: C: 46.43%, H: 4.96%, N: 40.95%
Calculated value: C: 46.60%, H: 4.89%, N: 40.75%
MS: 206(M+), 191, 149, 135

EXAMPLE 15

131.6 g (1.8 mol) of N,N-dimethylformamide and 42.8 g (0.36 mol) of thionyl chloride were added to 500 ml of 1,2-dichloroethane, and then 45.3 g (0.3 mol) of guanine (manufactured by Sumika Fine Chemicals Co., Ltd.) was added, followed by stirring at 80° C. for 6 hours. After cooling, the reaction mixture was added to 1000 ml of water to separate out the water layer, and then the water layer was neutralized with sodium hydrogen carbonate. The precipitating crystal was collected by filtration and washed with 100 ml of water to yield 52.6 g (0.255 mol) of a white crystal of N-dimethylaminomethyleneguanine (yield 85%).

EXAMPLE 16

20.6 g (0.1 mol) of N-dimethylaminomethyleneguanine obtained in Example 15, and 12.1 g (0.1 mol) of N,N-dimethylaniline were added to 38.3 g (0.25 mol) of phosphorus oxychloride, followed by stirring at 80° C. for 2 hours. After cooling, the reaction mixture was added to 500 ml of ice water, and then neutralized with 126.0 g (1.5 mol) of sodium hydrogen carbonate. The precipitating crystal was collected by filtration and then washed with 50 ml of water, subsequently with 50 ml of methanol to yield 18.0 g (0.08 mol) of a crystal of 2-dimethylaminomethyleneamino-6-chloropurine (yield 80%). Comparative Example (method disclosed in Japanese Patent Laid-Open No. 227583/1986)

4.5 g (0.03 mol) of guanine (manufactured by Sumika Fine Chemicals Co., Ltd.), 7.5 g (0.045 mol) of tetraethylammonium chloride and 27.1 g (0.177 mol) of phosphorus oxychloride were added to 60 ml of acetonitrile, followed by stirring for 70 minutes under heating refluxing conditions. After cooling, the crystal was collected by filtration and suspended in 50 ml of water. This suspension was made alakaline with a 30% aqueous solution of sodium hydroxide and then adjusted to a pH of 7 with 1N hydrochloric acid. The resulting crystal was collected by filtration and dissolved in 50 ml of 25% aqueous ammonia with heating, and the insoluble substances were filtered out. The mother liquor was concentrated under reduced pressure to yield 2.0 g (0.012 mol) of a precipitating crystal of 2-amino-6-chloropurine (yield 39%).

The present invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:
1. A. 2-formylamino-6-halogenopurine or a salt thereof represented by Formula (2):

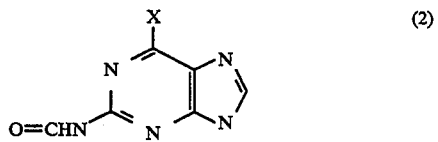

wherein X represents a chlorine atom, a bromine atom, an iodine atom or a fluorine atom.

* * * * *